United States Patent [19]

Inamoto et al.

[11] 4,272,536
[45] Jun. 9, 1981

[54] NOVEL TRICYCLOUNDECANE AMINOACID AMIDE

[75] Inventors: Yoshiaki Inamoto, Utsunomiya; Motoyoshi Osugi; Eiji Kashihara, both of Wakayama, all of Japan

[73] Assignees: Kao Soap Co., Ltd., Tokyo; Sumitomo Chemical Industries Ltd., Osaka, both of Japan

[21] Appl. No.: 102,674

[22] Filed: Dec. 12, 1979

[30] Foreign Application Priority Data

Dec. 21, 1978 [JP] Japan ................. 53-159541

[51] Int. Cl.³ .............. A61K 31/16; C07C 87/40; C07C 103/00
[52] U.S. Cl. .............. 424/248.54; 424/267; 424/274; 424/320; 544/154; 546/192; 260/326.2; 564/164; 564/165; 564/193
[58] Field of Search ......... 260/557 B, 326.2; 544/154; 546/192; 424/248–254, 267, 274, 320

[56] References Cited

U.S. PATENT DOCUMENTS

| | | | |
|---|---|---|---|
| 3,985,803 | 10/1976 | Inamoto et al. | 260/557 B |
| 4,104,305 | 8/1978 | Inamoto et al. | 260/563 P |

FOREIGN PATENT DOCUMENTS

| | | | |
|---|---|---|---|
| 2745193 | 4/1978 | Fed. Rep. of Germany | 260/557 B |
| 2745414 | 4/1978 | Fed. Rep. of Germany | 260/557 B |
| 53-50150 | 4/1978 | Japan | 260/557 |
| 53-63362 | 6/1978 | Japan | 260/557 B |

OTHER PUBLICATIONS

Koji et al., Chem. Abstracts, vol. 90, abst. 203,565u (1979) (abst. of Japan Kokai 79-14,953, Feb. 3, 1979).

Koji et al., Chem. Abstracts, vol. 90, abst. 203,567w (1979) (abst. of Japan Kokai 79-14,955, Feb. 3, 1979).

Inamoto et al., Chem. Abstracts, vol. 89, abst. 42588r (1978) (abst. of Ger. Offen. 2,745,414, Apr. 2, 1978).

*Primary Examiner*—John D. Randolph
*Attorney, Agent, or Firm*—Blanchard, Flynn, Thiel, Boutell & Tanis

[57] ABSTRACT

A compound having the formula

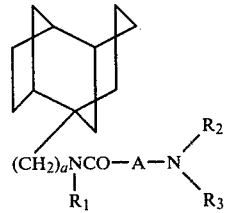

wherein $a$ is 0 or 1, $R_1$ is hydrogen or lower alkyl, A is lower alkylene or lower alkylidene, and $R_2$ and $R_3$, which can be the same or different, are hydrogen, lower alkyl, cycloalkyl, benzyl or substituted benzyl, or

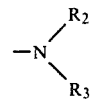

form a saturated heterocyclic ring, and pharmacologically acceptable acid addition salt thereof, exhibits antiviral activity and is free from significant effect on the central nervous system.

8 Claims, No Drawings

NOVEL TRICYCLOUNDECANE AMINOACID AMIDE

The present invention relates to aminoacid amides of amine derivatives of tricyclo[4.3.1.1$^{2,5}$]undecane and acid addition salts thereof. More particularly, the present invention relates to aminoacid amides of amine derivatives of tricyclo[4.3.1.1$^{2,5}$]undecane represented by the following general formula (I) and acid addition salts thereof:

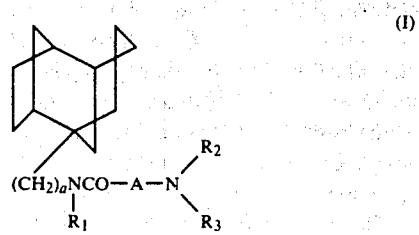

wherein a is 0 or 1, $R_1$ stands for a hydrogen atom or a lower alkyl group. A stands for a lower alkylene or lower alkylidene group, and $R_2$ and $R_3$, which can be the same or different, stand for a hydrogen atom, a lower alkyl group, a cycloalkyl group, a benzyl group or a substituted benzyl group, or they form a saturated heterocyclic ring together with the adjacent nitrogen atom.

It is known that some cage compounds have an anti-RNA-viral activity, but cage type compounds having an anti-DNA-viral activity are scarcely known and only tromantadine is known to have such activity (Japanese Patent Publication No. 32526/74). Recently, 1-aminotricyclo[4.3.1.1$^{2,5}$]undecane hydrochloride has been reported as a novel cage compound (Japanese patent application Laid-Open Specification No. 50150/78). However, it is known that the latter compound is only active against the Newcastle disease virus, which is one of the Paramyxo viruses belonging to the RNA viruses, in the chicken embryo cell in vitro test system. Derivatives of the latter compound have not been known.

We discovered novel tricyclo[4.3.1.1$^{2,5}$]undecane derivatives having an anti-viral activity not only against RNA viruses but also DNA viruses. We have now completed the present invention based on this discovery.

In accordance with the present invention, there are provided aminoacid amides of amine derivatives of tricyclo[4.3.1.1$^{2,5}$]undecane represented by the following general formula (I) and acid addition salts thereof:

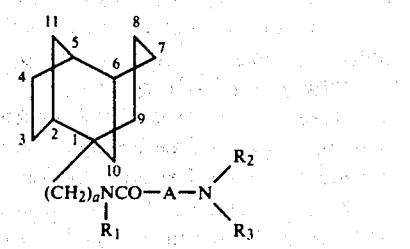

wherein a is 0 or 1, $R_1$ stands for a hydrogen atom or a lower alkyl group, A stands for a lower alkylene or lower alkylidene group, and $R_2$ and $R_3$, which can be the same or different, stand for a hydrogen atom, a lower alkyl group, a cycloalkyl group, a benzyl group or a substituted benzyl group, or they form a saturated heterocyclic ring together with the adjacent nitrogen atom.

In the general formula (I), $R_1$ stands for a hydrogen atom or a lower alkyl group. As the lower alkyl group, there can be mentioned, for example, alkyl groups having 1 to 4 carbon atoms, such as methyl, ethyl, propyl and butyl groups. It is preferred that $R_1$ is a hydrogen atom. $R_2$ and $R_3$ are defined as set forth above. As the lower alkyl group for $R_2$ and $R_3$, there can be mentioned, for example, alkyl groups having 1 to 4 carbon atoms, such as methyl, ethyl, propyl and butyl groups. As the cycloalkyl group, there can be mentioned, for example, 5-membered and 6-membered cycloalkyl groups such as cyclopentyl and cyclohexyl groups. As the substituted benzyl group, there can be mentioned, for example, benzyl groups in which the benzene ring is substituted with lower alkyl groups having 1 to 4 carbon atoms, lower alkoxy groups having 1 to 3 carbon atoms, halogen atoms such as chlorine and bromine, and a nitro group. Furthermore, $R_2$ and $R_3$ may form together with the adjacent nitrogen atom a saturated heterocyclic ring such as a pyrrolidine, piperidine or morpholine ring. The term "A" stands for a lower alkylene or lower alkylidene group. For example, there can be mentioned alkylene groups having 1 to 4 carbon atoms, such as methylene, ethylene, propylene and butylene groups, and alkylidene groups having 2 to 4 carbon atoms, such as ethylidene, propylidene and butylidene groups. The term a is 0 or 1, but a compound of the general formula (I) in which a is 0 is preferred because it is easily available.

Some examples of the compounds represented by the above general formula (I) are described below.

N-(1-tricyclo[4.3.1.1$^{2,5}$]undecyl)-2-aminoacetamide
N-(1-tricyclo[4.3.1.1$^{2,5}$]undecyl)-2-dimethylaminoacetamide
N-(1-tricyclo[4.3.1.1$^{2,5}$]undecyl)-2-diethylaminoacetamide
N-(1-tricyclo[4.3.1.1$^{2,5}$]undecyl)-2-cyclohexylaminoacetamide
N-(1-tricyclo[4.3.1.1$^{2,5}$]undecyl)-2-benzylaminoacetamide
N-(1-tricyclo[4.3.1.1$^{2,5}$]undecyl)-3-aminopropionamide
N-(1-tricyclo[4.3.1.1$^{2,5}$]undecyl)-3-diethylaminopropionamide
N-(1-tricyclo[4.3.1.1$^{2,5}$]undecyl)-3-benzylaminopropionamide
N-(1-tricyclo[4.3.1.1$^{2,5}$]undecyl)-3-cyclohexylaminopropionamide
N-(1-tricyclo[4.3.1.1$^{2,5}$]undecyl)-3-piperidinopropionamide
N-(1-tricyclo[4.3.1.1$^{2,5}$]undecyl)-2-aminopropionamide
N-methyl-N-(1-tricyclo[4.3.1.1$^{2,5}$]undecyl)-2-aminoacetamide
N-methyl-N-(1-tricyclo[4.3.1.1$^{2,5}$]undecyl)-2-cyclohexylaminoacetamide
N-methyl-N-(1-tricyclo[4.3.1.1$^{2,5}$]undecyl)-3-aminopropionamide
N-methyl-N-(1-tricyclo[4.3.1.1$^{2,5}$]undecyl)-3-cyclohexylaminopropionamide The compounds of the present invention represented by the general formula (I) can be prepared by reacting a tricyclo[4.3.1.1$^{2,5}$]undecanamide halide represented by the following general formula (II):

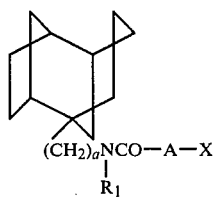

$$(CH_2)_a NCO-A-X \atop R_1 \qquad (II)$$

wherein a, $R_1$ and A are as defined above, and X stands for a halogen atom selected from chlorine, bromine and iodine, with an amine represented by the following general formula (III):

wherein $R_2$ and $R_3$ are as defined above.

As specific examples of the amine represented by the general formula (III), there can be mentioned ammonia, methylamine, ethylamine, propylamine, butylamine, dimethylamine, diethylamine, dipropylamine, dibutylamine, cyclohexylamine, benzylamine, methoxybenzylamine, piperidine and morpholine.

It is preferred that the reaction be carried out in an inert organic solvent. Any organic solvents inactive to the reaction can be used. As organic solvents that can be advantageously used, there can be mentioned, for example, lower alcohols such as methanol, ethanol and propanol, chlorinated hydrocarbons such as methylene chloride, chloroform and carbon tetrachloride, and aromatic hydrocarbons such as benzene, toluene and xylene. It is preferred that the compound of the formula (III) be used in an amount of about 1 to 4 moles per mole of the compound of the formula (II). The reaction is conducted at a temperature in the range of from room temperature to a temperature approximating the boiling point of the solvent used. It is preferred that the reaction be carried out at a temperature approximating the boiling point of the solvent used. The reaction is ordinarily completed within 3 to 10 hours.

A compound of the general formula (I) in which each of $R_2$ and $R_3$ is a hydrogen atom can be prepared according to the above-mentioned method, but it sometimes happens that by-products are formed when the above-mentioned method is adopted. In such case, there can be employed a method in which a compound of the formula (II) is first reacted with potassium phthalimide to form a phthalimide derivative and the derivative is then decomposed by hydrazine or an alkali such as sodium hydroxide, potassium hydroxide or barium hydroxide, whereby the intended primary amine derivative [$R_2=R_3=H$ in the formula (I)] can easily be prepared. According to this method, the formation of by-products is remarkably reduced. In this method, potassium phthalimide is used in an amount of 1 to 2 moles, preferably 1.1 to 1.3 moles, per mole of the compound of the formula (II). As the solvent, there are employed glycols such as ethylene glycol, chlorinated hydrocarbons such as methylene chloride and chloroform, and dimethylformamide (DMF). Dimethylformamide is especially preferred because the reaction time is shortened and the yield is improved. The reaction is carried out at a temperature of 30° to 160° C., preferably 100° to 130° C. Decomposition of the phthalimide derivative is performed in an aqueous solution of an alkali at 50° to 100° C., preferably 80° to 100° C. or in an ethanol solution of hydrazine at 50° to 80° C., preferably 70° to 80° C., whereby the intended primary amine derivative [$R_2=R_3=H$ in the formula (I)] can easily be prepared. Hydrazine is used in an amount of 1 to 3 moles, preferably 1 to 1.5 moles, per mole of the phthalimide derivative.

Furthermore, a compound of the formula (I) in which $R_2$ and $R_3$ stand for a hydrogen atom can be prepared according to a method in which a compound of the formula (I) in which $R_2$ is a hydrogen atom and $R_3$ is a benzyl or substituted benzyl group is first prepared and this compound is hydrogenolyzed. Hydrogenolysis may be carried out under conditions (catalyst, temperature and hydrogen pressure) customarily adopted in hydrogenation.

The acid addition salt of the compound of the formula (I) can easily be prepared by neutralizing the thus-obtained compound of the formula (I) with an acid. Either a mineral acid or an organic acid can be used for this neutralization. As the mineral acid, there can be mentioned, for example, hydrohalogenic acids (hydrogen halides) such as hydrochloric acid, hydrobromic acid and hydroiodic acid, phosphoric acid, pyrophosphoric acid, sulfuric acid, thiosulfuric acid and boric acid. As the organic acid, there can be mentioned, for example, fatty acids such as formic acid, acetic acid, propionic acid, butyric acid, capric acid and lauric acid, saturated dibasic acids such as oxalic acid, malonic acid, succinic acid, glutaric acid and adipic acid, aliphatic hydroxyacids such as glycolic acid, malic acid, lactic acid, tartaric acid and citric acid, halogenated acetic acids such as monochloroacetic acid and monobromoacetic acid, and aromatic carboxylic acids such as benzoic acid, salicylic acid, p-hydroxybenzoic acid, m-hydroxybenzoic acid, phthalic acid and terephthalic acid. In addition to these carboxylic acids, there can be employed organic sulfonic acids such as methane-sulfonic acid, ethane-sulfonic acid, benzene-sulfonic acid and p-toluene-sulfonic acid. Among these acids, a hydrohalogenic acid, especially hydrochloric acid, is preferred because its handling is very easy. The acid addition salt can be prepared according to customary methods, for example, a method in which the compound of the formula (I) is neutralized by a solution containing an acid as mentioned above and the mixture is dried to the solid, or a method in which an acid is added to a solution of the compound of the formula (I) in diethyl ether, chloroform, carbon tetrachloride or the like, and the formed precipitate of the acid addition salt is recovered by filtration. When the acid is hydrochloric acid, it is preferred to adopt a method in which dry hydrogen chloride gas is blown into a solution of the compound of the formula (I) and the formed precipitate is recovered by filtration.

The starting halide compound of the formula (II) is prepared by reacting an amine represented by the following formula (IV):

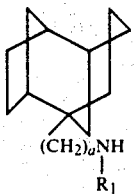

wherein a and $R_1$ are as defined above, with a halogenocarboxylic acid halide represented by the following general formula (VI):

X'-CO-A-X  (VI)

wherein A and X are the same as defined above, and X' stands for a halogen atom selected from chlorine, bromine and iodine, in the presence of a base, in an inert organic solvent. Any organic solvent inactive to the reaction can be used. Preferred solvents include, for example, aromatic hydrocarbons such as benzene, toluene and xylene, linear hydrocarbon solvents such as pentane and hexane, and chlorinated hydrocarbon solvents such as methylene chloride, chloroform and carbon tetrachloride. As the base that is used for this reaction, there can be mentioned, for example, alkali metal carbonates such as sodium carbonate and potassium carbonate, and tertiary amines such as pyridine and triethylamine. It is preferred that the halogenocarboxylic acid halide be used in an amount of 1 to 1.2 moles per mole of the amine of the formula (IV) and the base be used in an amount of 1 to 1.2 moles per mole of the amine of the formula (IV).

The process for the formation of an amine (primary amine) of the formula (IV) in which a is 0 and $R_1$ is a hydrogen atom (1-aminotricyclo[4.3.1.1$^{2,5}$]undecane) is disclosed in Japanese patent application Laid-Open Specification No. 50150/78. The compound of the formula (IV) in which a is 1 and $R_1$ is a hydrogen atom may be prepared from a known substance according to the following reactions:

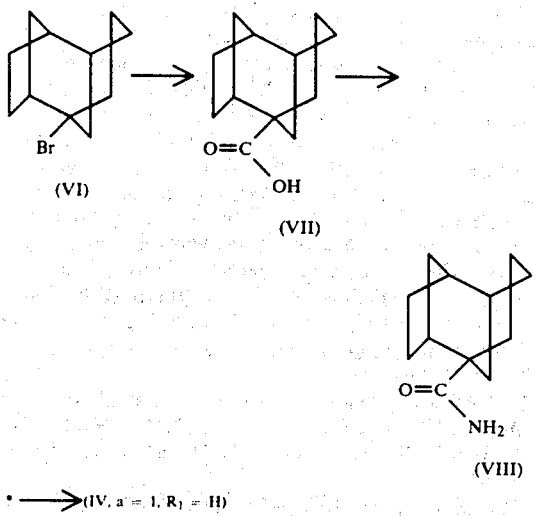

More specifically, the bromide (VI, disclosed in Japanese patent application Laid-Open Specification No. 46949/78) is reacted with formic acid in the presence of sulfuric acid to form a carboxylic acid (VII), the carboxylic acid (VII) is reacted with ammonia to form an acid amide (VIII), and the acid amide (VIII) is reduced by customary procedures to obtain an amine (IV, a=1, $R_1$=H). The amine of the formula (IV) in which $R_1$ is a lower alkyl group is prepared by alkylating the above-mentioned primary amine (IV, $R_1$=H) with a lower alkyl halide such as methyl iodide or butyl iodide or by converting the primary amine to an acid amide with a lower fatty acid and reducing the acid amide.

The aminoacid amide compound of the present invention represented by the general formula (I) and its acid addition salt have an excellent anti-viral activity not only to RNA virus, but also to herpes virus which is a DNA virus. They do not show any side effects on the central nervous system. Accordingly, they are very valuable as medicines for treatment of virus-caused diseases and as anti-viral agents for animals.

The present invention will now be described in detail by reference to the following Examples that by no means limit the scope of the invention.

EXAMPLE 1

Preparation of N-(1-tricyclo[4.3.1.1$^{2,5}$]undecyl)-3-diethylaminopropionamide hydrochloride (A) Preparation of N-(1-tricyclo[4.3.1.1$^{2,5}$]undecyl)-3-chloropropionamide:

A solution of 2.55 g (20.1 millimoles) of 3-chloropropionyl chloride in 75 ml of dry diethyl ether was added dropwise to a liquid mixture of 3.00 g (18.3 millimoles) of 1-aminotricyclo[4.3.1.1$^{2,5}$]undecane, 75 ml of chloroform, 2.13 g (20.1 millimoles) of sodium carbonate and 18 ml of water, under ice cooling and with stirring, over a period of 30 minutes. The mixture was further stirred for 2 hours, and the aqueous layer was separated from the organic layer and extracted with 100 ml of chloroform. The organic extract was combined with the organic layer, and the mixture was washed with a saturated aqueous solution of sodium chloride and dried. The solvent was removed by distillation to obtain 4.60 g (the yield being 98.3%) of white crystals of the intended compound.

Melting point: 156°–159° C.

Elementary analysis values: Calculated as $C_{14}H_{22}ClNO$: C=65.75%, H=8.61%, N=5.48%, Cl=13.90%. Found: C=65.2%, H=8.9%, N=5.5%, Cl=13.0%.

IR (nujol), cm$^{-1}$: 3290, 3060, 1640, 1550.

$^1$HNMR (CDCl$_3$), δ: 1.1–2.1 (m, 17H), 2.5 (t, 2H, —COCH$_2$CH$_2$—), 3.77 (t, 2H, —COCH$_2$CH$_2$—), 5.7 (bs, 1H, —NHCO—).

(B) Preparation of N-(1-tricyclo[4.3.1.1$^{2,5}$]undecyl)-3-diethylaminopropionamide hydrochloride:

A solution of 1.58 g (6.18 millimoles) of N-(1-tricyclo[4.3.1.1$^{2,5}$]undecyl)-3-chloropropionamide obtained as described above and 0.59 g (8.03 millimoles) of diethylamine in 50 ml of anhydrous ethanol was mixed with 10 ml of an aqueous solution containing 0.52 g (6.18 millimoles) of sodium hydrogencarbonate and 0.10 g (0.62 millimole) of potassium iodide, and the mixture was refluxed under stirring for 16 hours. The liquid reaction mixture was condensed, mixed with a 5% aqueous solution of sodium hydroxide and extracted with diethyl ether. The extract was washed with water and dried and the solvent was removed by distillation. The residue was dissolved in 20 ml of dry diethyl ether and dry hydrogen chloride was blown into the solution, and the formed precipitate was recovered by filtration. The precipitate was recrystallized from acetone-methanol to obtain 1.05 g (the yield being 51.7%) of white crystals of the intended compound having a melting point of 192°–195° C.

Elementary analysis values: Calculated as $C_{18}H_{33}ClN_2O$: C=65.75%, H=10.05%, N=8.52%, Cl=10.81%. Found: C=65.5%, H=10.4%, N=8.3%, Cl=10.5%.

IR (nujol), cm$^{-1}$: 3260, 3060, 2900, 2600, 2500, 1660, 1550, 1460.

MS, m/e (relative intensity): 293 (1.1), 292 (4.4), 176 (37.4), 150 (99.8), 122 (34.1), 96 (99.8), 86 (100).

$^1$HNMR* (CDCl$_3$), δ: 1.0 (t, 6H, —CH$_2$C$\underline{H}$$_3$), 2.56 (q, 4H, —C$\underline{H}$$_2$CH$_3$), 1.3–2.5 (m, 22H), 8.67 (bs, 1H, —N$\underline{H}$CO—).

*: measured with respect to the free amine

EXAMPLE 2

Preparation of N-(1-tricyclo[4.3.1.1$^{2,5}$]undecyl)-3-piperidinopropionamide hydrochloride To a solution of 1.00 g (3.91 millimoles) of N-(1-tricyclo[4.3.1.1$^{2,5}$]undecyl)-3-chloropropionamide and 0.33 g (3.91 millimoles) of piperidine in 20 ml of diethyl ether was added 6 ml of an aqueous solution containing 0.27 g (3.91 millimoles) of sodium hydrogencarbonate and 0.065 g (0.39 millimole) of potassium iodide, and the mixture was refluxed under stirring for 6 hours. The post treatment was carried out in the same manner as described in Example 1 to obtain 1.00 g (the yield being 75%) of the intended compound having a melting point of 207° to 212° C.

Elementary analysis values: Calculated as $C_{19}H_{33}ClN_2O$: C=66.96%, H=9.69%, N=8.22%, Cl=10.43%. Found: C=66.5%, H=9.2%, N=8.2%, Cl=10.0%.

IR (nujol), cm$^{-1}$: 3230, 3200, 3050, 2930, 2610, 2380, 1650, 1550, 1460.

$^1$HNMR* (CDCl$_3$), δ: 1.33–2.17 (m, 23H), 2.17–2.67 (m, 8H).

*: as measured with respect to the free amine MS, m/e (relative intensity): 305 (5), 304 (23), 150 (100), 122 (35), 112 (30), 98 (98), 96 (100).

EXAMPLE 3

Preparation of N-(1-tricyclo[4.3.1.1$^{2,5}$]undecyl)-3-aminopropionamide hydrochloride (A) Preparation of N-(1-tricyclo[4.3.1.1$^{2,5}$]undecyl)-3-benzylaminopropionamide:

To a solution of 1.40 g (5.47 millimoles) of N-(1-tricyclo[4.3.1.1$^{2,5}$]undecyl)-3-chloropropionamide and 0.59 g (5.47 millimoles) of benzylamine in 30 ml of ethanol was added 7 ml of an aqueous solution containing 0.46 g (5.47 millimoles) of sodium hydrogencarbonate and 0.091 g (0.54 millimole) of potassium iodide, and the mixture was refluxed under agitation. The post treatment was carried out in the same manner as described in section (B) of Example 1 to obtain 1.04 g (the yield being 58%) of oily N-(1-tricyclo[4.3.1.1$^{2,5}$]undecyl)-3-benzylaminopropionamide.

Elementary analysis values: Calculated as $C_{21}H_{30}N_2O$: C=77.30%, H=9.20%, N=8.59%. Found: C=77.0%, H=8.9%, N=9.0%.

IR (liquid film), cm$^{-1}$: 3280, 3040, 3010, 2910, 2850, 1640, 1540, 905.

$^1$HNMR (CDCl$_3$), δ: 1.33–2.5 (m, 19H), 2.83 (2H, —CH$_2$C$\underline{H}$$_2$NH—), 3.75 (s, 2H, 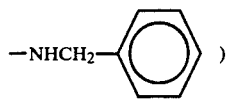)

7.0 (bs, 1H, —N$\underline{H}$CO—), 7.23 (s, 5H, benzene nucleus).

(B) Preparation of N-(1-tricyclo[4.3.1.1$^{2,5}$]undecyl)-3-aminopropionamide hydrochloride:

To a solution of 1.04 g (3.19 millimoles) of crude N-(1-tricyclo[4.3.1.1$^{2,5}$]undecyl)-3-benzylaminopropionamide in 20 ml of acetic acid was added 0.25 g of 5% palladium on carbon catalyst, and hydrogenation was carried out at 70° C. under 15 atmospheres hydrogen pressure for about 10 hours. The palladium-carbon catalyst was removed by filtration and the acetic acid solution was concentrated under reduced pressure. The residue was dissolved in anhydrous benzene and dry hydrogen chloride gas was blown into the solution, and the formed precipitate was recovered by filtration and recrystallized from acetone-methanol to obtain 810 mg (the yield being 91%) of the intended compound in the form of crystals having a melting point of 138° to 140° C.

Elementary analysis values: Calculated as $C_{14}H_{25}ClN_2O$: C=61.64%, H=9.24%, N=10.27%, Cl=13.00%. Found: C=57.9%, H=9.4%, N=9.8%, Cl=11.9%.

IR (nujol), cm$^{-1}$: 3500, 3350, 2900, 1660, 1540, 1490, 1460, 1370, 1220.

$^1$HNMR (D$_6$-DMSO), δ: 1.2–2.2 (m, 19H), 3.38 (bs, 2H), 3.8 (bs, 1H, —N$\underline{H}$CO—), 8.16 (bs, 2H, —CH$_2$NH$_2$).

MS, m/e (relative intensity): 220 (5), 219 (30), 96 (50), 44 (100).

EXAMPLE 4

Preparation of N-(1-tricyclo[4.3.1.1$^{2,5}$]undecyl)-2-cyclohexylaminoacetamide hydrochloride (A) Preparation of N-(1-tricyclo[4.3.1.1$^{2,5}$]undecyl)-2-chloroacetamide:

2.55 g (20.1 millimoles) of 2-chloroacetyl chloride was added dropwise to a liquid mixture of 3.00 g (18.3 millimoles) of 1-aminotricyclo[4.3.1.1$^{2,5}$]undecane, 75 ml of chloroform, 2.13 g (20.1 millimoles) of sodium carbonate and 20 ml of water, under ice cooling and with stirring, over a period of 30 minutes. The mixture was further stirred for 2 hours, and the aqueous layer was separated from the organic layer and extracted with 30 ml of chloroform. The organic extract was combined with the organic layer, and the mixture was washed with a saturated aqueous solution of sodium chloride and dried. The solvent was removed by distillation to obtain 3.19 g (the yield being 72.2%) of white crystals of the intended compound having a melting point of 130° to 135° C.

Elementary analysis values: Calculated as $C_{13}H_{20}ClNO$: C=64.59%, H=8.34%, N=5.79%, Cl=14.66%. Found: C=63.4%, H=8.7%, N=5.5%, Cl=14.0%.

IR (nujol), cm$^{-1}$: 3300, 3070, 2930, 1640, 1550, 1470, 1340, 1255.

$^1$HNMR (CDCl$_3$), δ: 1.3–2.66 (m, 17H), 3.9 (s, 2H, —COC$\underline{H}$$_2$Cl), 6.2 (bs, 1H, —N$\underline{H}$CO—).

MS, m/e (relative intensity): 241 (4.4), 198 (39), 172 (100), 96 (34), 67 (25).

(B) Preparation of N-(1-tricyclo[4.3.1.1$^{2,5}$]undecyl)-2-cyclohexylaminoacetamide hydrochloride:

A solution of 1.20 g (4.96 millimoles) of N-(1-tricyclo[4.3.1.1$^{2,5}$]undecyl)-2-chloroacetamide and 0.49 g (4.96 millimoles) of cyclohexylamine in ethanol was mixed with 5 ml of an aqueous solution containing 0.42 g (4.96 millimoles) of sodium hydrogencarbonate and 8.2 mg (0.49 millimole) of potassium iodide, and the mixture was refluxed, under agitation, for 15 hours. The post treatment was carried out in the same manner as described in section (B) of Example 1 to obtain 1.01 g (the yield being 59.8%) of white crystals of the intended compound having a melting point of 192°-195° C. (recrystallized from methanol-acetone).

Elementary analysis values: Calculated as $C_{19}H_{33}ClN_2O$: C=66.96%, H=9.69%, N=8.22%, Cl=10.42%. Found: C=66.3%, H=9.1%, N=8.1%, Cl=10.5%.

IR (nujol), cm$^{-1}$: 3175, 3040, 2900, 2830, 1670, 1560, 1440.

MS, m/e (relative intensity): 304 (6), 149 (12), 113 (57), 112 (98), 98 (100), 96 (44), 83 (38).

$^1$HNMR* (CDCl$_3$), δ: 1.3-2.57 (m, 29H), 3.07 (s, 2H, —COC$\underline{H}_2$N—), 7.1 (bs, —N$\underline{H}$CO—).

*: measured with respect to the free amine

EXAMPLE 5

Preparation of N-(1-tricyclo[4.3.1.1$^{2,5}$]undecyl)-2-benzylacetamide hydrochloride To a solution of 1.20 g (4.96 millimoles) of N-(1-tricyclo[4.3.1.1$^{2,5}$]undecyl)-2-chloroacetamide and 0.49 g (4.96 millimoles) of benzylamine in 40 ml of ethanol was added 20 ml of an aqueous solution containing 0.42 g (4.96) millimoles) of sodium hydrogencarbonate and 82.3 mg (0.496 millimole) of potassium iodide, and the mixture was refluxed, under agitation, for 15 hours. The post treatment was carried out in the same manner as described in section (B) of Example 1 to obtain 0.60 g (the yield being 35%) of the intended compound having a melting point of 228° to 229° C. (recrystallized from methanolacetone).

Elementary analysis values: Calculated as $C_{20}H_{29}ClN_2O$: C=68.86%, H=8.32%, N=8.03%, Cl=10.18%. Found: C=68.2%, H=8.7%, N=8.0%, Cl=10.3%. IR (nujol), cm$^{-1}$: 3240, 3050, 2900, 2850, 2670, 1670, 1550, 1450, 1400.

$^1$HNMR* (CDCl$_3$), δ: 1.33-2.6 (m, 18H), 3.08 (s, 2H, —COC$\underline{H}_2$N—) 3.68 (s, 2H, —NHC$\underline{H}_2$C$_6$H$_5$) 7.0 (bs, 1H, —N$\underline{H}$CO) 7.27 (s, 5H, benzene nucleus).

*: as measured with respect to the free amine

MS, m/e (relative intensity): 312 (4), 311 (13), 207 (61), 164 (22), 149 (33), 138 (76), 121 (71), 120 (90), 107 (61), 106 (100).

EXAMPLE 6

Preparation of N-(1-tricyclo[4.3.1.1$^{2,5}$]undecyl)-2-piperidinoacetamide hydrochloride To a solution of 1.50 g (6.2 millimoles) of N-(1-tricyclo[4.3.1.1$^{2,5}$]undecyl)-2-chloroacetamide and 0.53 g (6.2 millimoles) of piperidine in 50 ml of ethanol was added 10 ml of an aqueous solution containing 0.52 g (6.2 millimoles) of sodium hydrogencarbonate and 0.10 g (0.62 millimole) of potassium iodide, and the mixture was refluxed, under agitation, for 10 hours. The post treatment was carried out in the same manner as described in section (B) of Example 1 to obtain 1.63 g (the yield being 81%) of the intended compound having a melting point of 174° to 176° C. (recrystallized from methanolacetone).

Elementary analysis values: Calculated as $C_{18}H_{31}ClN_2O$: C=66.13%, H=9.56%, N=8.57%, Cl=10.85%. Found: C=65.2%, H=9.7%, N=8.3%, Cl=10.8%.

IR (nujol), cm$^{-1}$: 3250, 3225, 2925, 1680, 1550, 1470, 1380, 1365, 1200, 950. $^1$HNMR* (CDCl$_3$), δ: 1.3-2.6 (m, 27H), 2.8 (s, 2H, —COC$\underline{H}_2$N), 7.0 (bs, 1H, —N$\underline{H}$CO—).

*: as measured with respect to the free amine

MS, m/e (relative intensity): 289 (5), 98 (100).

EXAMPLE 7

Preparation of N-(1-tricyclo[4.3.1.1$^{2,5}$]undecyl)-2-aminoacetamide hydrochloride (A) A liquid mixture of 1.50 g (6.2 millimoles) of N-(1-tricyclo[4.3.1.1$^{2,5}$]undecyl)-2-chloroacetamide, 1.38 g (7.4 millimoles) of potassium phthalimide and 15 ml of dimethylformamide was refluxed, under agitation, for 12 hours. After cooling, 20 ml of water was added and the mixture was extracted 3 times with 20 ml of chloroform. The organic extract was washed with a 5% aqueous solution of sodium hydroxide and then with water. The chloroform solution was dried and the solvent was removed by distillation to obtain 1.39 g (the yield being 55%) of N-(1-tricyclo[4.3.1.1$^{2,5}$]undecyl)-2-phthalimidoacetamide in the form of a semi-solid.

IR (nujol), cm$^{-1}$: 1775, 1725, 1675, 1615.

(B) A mixture of 1.39 g (3.94 millimoles) of N-(1-tricyclo[4.3.1.1$^{2,5}$]undecyl)-2-phthalimidoacetamide, 0.30 g (4.37 millimoles) of 80% hydrazine hydrate and 10 ml of ethanol was refluxed under agitation for 4 hours. The reaction temperature was lowered to 60° C., and 5 ml of 10% hydrochloric acid was added and the mixture was agitated for 2 hours. After cooling, the precipitate was recovered by filtration, and the pH of the filtrate was adjusted to 9 with a 5% aqueous solution of sodium hydroxide and the mixture was extracted with diethyl ether. The diethyl ether solution was condensed, and the residue was dissolved in 20 ml of dry benzene and dry hydrogen chloride gas was blown into the solution. The formed white precipitate was recovered by filtration and recrystallized from ethanolacetone to obtain 0.59 g (the yield being 58%) of the intended compound having a melting point of 225° to 229° C.

Elementary analysis values: Calculated as $C_{13}H_{23}ClN_2O$: C=60.34%, H=8.96%, N=10.82%, Cl=13.70%. Found: C=59.6%, H=9.2%, N=10.9%, Cl=12.9%.

IR (nujol), cm$^{-1}$: 3220, 2900, 2640, 1660, 1550, 1510, 1460, 1370, 1270, 890.

$^1$HNMR* (CDCl$_3$), δ: 1.26-2.56 (m, 19H), 3.1 (bs, 2H, —N$\underline{H}_2$), 7.0 (bs, 1H, —N$\underline{H}$CO—).

*: measured with respect to the free amine

MS, m/e (relative intensity): 222 (11), 205 (76), 154 (26), 153 (100), 149 (33), 122 (66).

EXAMPLE 8

Preparation of N-methyl-N-(1-tricyclo[4.3.1.1$^{2,5}$]undecyl)-2-aminoacetamide hydrochloride (A) Preparation of N-(1-tricyclo[4.3.1.1$^{2,5}$]undecyl)formamide:

10 ml of anhydrous acetic acid was added to 2.72 g of 1-aminotricyclo[4.3.1.1$^{2,5}$]undecane formate and the mixture was agitated for 40 minutes. 20 ml of water was added to the reaction mixture, and the resulting mixture was heated at 80° C. for 1 hour. After cooling, the reaction mixture was neutralized with sodium carbonate and extracted with diethyl ether. The diethyl ether solution was dried and condensed to obtain 2.20 g (the yield being 92%) of N-(1-tricyclo[4.3.1.1$^{2,5}$]undecyl)-formamide.

Elementary analysis values: Calculated as $C_{12}H_{19}NO$: C=74.57%, H=9.91%, H=7.25%. Found: C=74.5%, H=10.0%, N=7.7%.

IR (neat), cm$^{-1}$: 3250, 3030, 2925, 2860, 1700, 1660, 1540, 1380, 1360, 1270.

$^1$HNMR (CDCl$_3$), δ: 1.4–2.57 (m, 17H), 8.2 (bs, 1H, —NHCOH), 9.4 (bs, 1H, —CHO).

MS, m/e (relative intensity): 193 (12, M+), 150 (44), 124 (100), 96 (23).

(B) Preparation of 1-methylaminotricyclo[4.3.1.1$^{2,5}$]undecane:

A solution of 2.38 g (12.3 millimoles) of N-(1-tricyclo[4.3.1.1$^{2,5}$]undecyl)-formamide in 25 ml of dry tetrahydrofuran was added dropwise to a suspension of 1.36 g (35.9 millimoles) of lithium aluminum hydride in 70 ml of dry diethyl ether under reflux and agitation. After completion of the dropwise addition, the mixture was refluxed for 5 hours. After cooling, 1.36 ml of water, 1.36 ml of a 3 N aqueous solution of sodium hydroxide and 4.08 ml of water were added dropwise in sequence to the reaction mixture. The formed precipitate was removed by filtration, and the filtrate was condensed and the residue was subjected to fractional distillation to obtain 1.51 g (the yield being 73%) of a fraction boiling at 123° C. under 13 mmHg.

Elementary analysis values: Calculated as $C_{12}H_{21}N$: C=80.38%, H=11.81%, N=7.81%. Found: C=80.0%, H=11.2%, N=7.9%.

IR (neat), cm$^{-1}$: 3250, 3025, 2925, 2860, 1675, 1550, 1480.

$^1$HNMR (CDCl$_3$), δ: 1.0–2.1 (m, 18H), 2.2 (m, 3H, —CH$_3$).

MS, m/e (relative intensity): 179 (5, M+), 138 (11), 136 (32), 110 (100).

(C) Preparation of N-methyl-N-(1-tricyclo[4.3.1.1$^{2,5}$]undecyl)-2-chloroacetamide:

Under the same conditions as described in section (A) of Example 4, 1-methylaminotricyclo[4.3.1.1$^{2,5}$]undecane was reacted with 2-chloroacetyl chloride to obtain N-methyl-N-(1-tricyclo[4.3.1.1$^{2,5}$]undecyl)-2-chloroacetamide in a yield of 85%.

Elementary analysis values: Calculated as $C_{14}H_{22}ClNO$: C=65.74%, H=8.67%, N=5.48%, Cl=13.86%. Found: C=65.5%, H=8.8%, N=5.8%, Cl=13.4%.

IR (nujol), cm$^{-1}$: 2900, 2850, 1640, 1470, 1380, 1100.

$^1$HNMR (CDCl$_3$), δ: 1.27–2.17 (m, 17H), 3.00 (s, 3H, —N—CH$_3$), 4.07 (s, 2H, CH$_2$).

MS, m/e (relative intensity): 257 (3.8, M+), 255 (9.4, M+), 220 (31), 188 (34), 186 (100), 110 (57), 90 (70), 67 (50).

(D) Preparation of N-methyl-N-(1-tricyclo[4.3.1.1$^{2,5}$]undecyl)-2-phthalimidoacetamide:

Under the same reaction conditions as described in section (A) of Example 7, N-methyl-N-(1-tricyclo[4.3.1.1$^{2,5}$]undecyl)-2-chloroacetamide was reacted with potassium phthalimide to obtain N-methyl-N-(1-tricyclo[4.3.1.1$^{2,5}$]undecyl)-2-phthalimidoacetamide in a yield of 83%.

Elementary analysis values: Calculated as $C_{22}H_{26}N_2O_3$: C=72.10%, H=7.15%, N=7.65%. Found: C=73.0%, H=7.35%, N=7.80%.

IR (neat), cm$^{-1}$: 3000, 2900, 2850, 1775, 1710, 1680, 1640, 1460, 1420, 1380, 1105, 960, 820.

$^1$HNMR (CDCl$_4$), δ: 1.33–2.0 (m, 17H), 3.0 (s, 3H, N—CH$_3$), 4.4 (s, 2H, —CH$_2$—), 7.76 (4H, benzene nucleus).

MS, m/e (relative intensity): 367 (4), 366 (9, M+), 297 (34), 161 (100), 160 (59), 133 (32), 120 (36).

(E) Preparation of N-methyl-N-(1-tricyclo[4.3.1.1$^{2,5}$]undecyl)-2-aminoacetamide hydrochloride:

Under the same reaction conditions as described in section (B) of Example 7, N-methyl-N-(1-tricyclo[4.3.1.1$^{2,5}$]undecyl)-2-phthalimidoacetamide was reacted with 80% hydrazine hydrate to split off the phthalyl group, and the reaction product was neutralized by blowing of hydrogen chloride gas to obtain N-methyl-N-(1-tricyclo[4.3.1.1$^{2,5}$]undecyl)-2-aminoacetamide hydrochloride having a melting point exceeding 300° C. in a yield of 52% (recrystallized from methanol-acetone).

Elementary analysis values: Calculated as $C_{14}H_{24}ClN_2O$: C=61.65%, H=9.17%, N=10.27%, Cl=13.02% Found: C=61.85%, H=10.3%, N=10.2%, Cl=12.8%.

IR* (liquid film), cm$^{-1}$: 3700-3100, 2925, 2860, 1640, 1470, 1390, 1270, 1245, 780, 755.

$^1$HNMR* (CDCl$_3$), δ: 1.33–2.6 (m, 19H), 2.83 (s, 3H, N—CH$_3$), 3.2 (bs, 2H, —NH$_2$).

MS, m/e (relative intensity)*: 195 (3), 179 (5), 138 (15), 119 (24), 117 (24), 110 (100), 96 (27).

*: measured with respect to the free amine

EXAMPLE 9

Preparation of N-(1-tricyclo[4.3.1.1$^{2,5}$]undecyl)-2-aminopropionamide hydrochloride Under the same conditions as described in sections (D) and (E) of Example 8, N-(1-tricyclo[4.3.1.1$^{2,5}$]undecyl)-2-chloropropionamide was converted to the phthalimide derivative, the derivative was converted to an amine by 80% hydrazine hydrate and the amine was neutralized by hydrogen chloride gas to obtain viscous N-(1-tricyclo[4.3.1.1$^{2,5}$]undecyl)-2-aminopropionamide hydrochloride in a yield of 32%.

Elementary analysis values: Calculated as $C_{14}H_{25}ClN_2O$: C=61.65%, H=9.17%, N=10.27%, Cl=13.02%. Found: C=59.8%, H=9.4%, N=9.8%, Cl=12.3%.

IR (KBr), cm$^{-1}$: 3600-3200, 2900, 1630, 1540, 1460, 1150, 1105.

MS, m/e (relative intensity): 236 (6), 167 (42), 150 (25), 122 (37), 96 (100), 67 (14).

PHARMACOLOGICAL EXAMPLE

The anti-viral activity was tested in vivo by using mice infected with mouse-tamed A/PR/8/34 (HONI) influenza virus. The results obtained are shown in Table.

TABLE

| | Anti-Influenzal Action | | |
|---|---|---|---|
| compound tested | amount administered (mg/kg) | survival ratio | LLS value |
| N-(1-tricyclo[4.3.1.1$^{2,5}$]-undecyl)-2-aminoacetamide hydrochloride | 15 | 4/10 | 4.10 |
| Amantadine hydrochloride | 50 | 3/10 | 4.45 |
| control | — | 2/10 | 4.6 |

Virus:
Mouse-tamed A/PR/8/34 (HONI) influenza virus
Animal:
Male mice of the ddy system, 3 weeks old, body weight of 12-13 g.
Infection with virus:
Method of Kashiwagi et al. [*Journal of Medicine of Fukuoka*, 65 (3), 157-171 (1974)].
Administration of compounds:
The test compound was dissolved in physiological saline solution, and 0.1 ml of the solution was subcutaneously injected. The concentration of the compound was adjusted so that the amount shown in the above shown table was administered to the mouse having a body weight of 12 g. Administration was continued in the same amount irrespective of the change of the body weight. On the day when infection was performed, the solution was administered 3 times, that is, 2 hours before the infection, 2 hours after the infection and 6 hours after the infection, and the administration was conducted at intervals of 12 hours for subsequent 6 days.
Lung Lesion score (LLS value):
The mice that died during the experiment were anatomized when they died and the surviving mice were killed on the 7th day and anatomized. The LLS value was determined according to the method of Tani et al. [*Journal of Medicine of Fukuoka*, 58, (9), 801-815 (1967)]. Each of the LLS values in the above shown table is an average value for the total mice tested.
Survival ratio:
The survival ratio is expressed in terms of the ratio of the number of mice that survived to the 7th day to the total number of mice tested.

The embodiments of the invention in which an exclusive property or privilege is claimed are defined as follows:

1. A compound having the formula

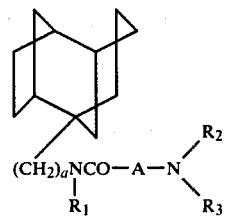

$$(CH_2)_a NCO-A-N\begin{matrix}R_2\\ \\R_3\end{matrix}$$
$$\phantom{(CH_2)_a NCO-A-N}|$$
$$\phantom{(CH_2)_a NCO-A-}R_1$$

(I)

wherein a is 0 or 1, $R_1$ is hydrogen or lower alkyl having from 1 to 4 carbon atoms, A is lower alkylene having from 1 to 4 carbon atoms or lower alkylidene having from 2 to 4 carbon atoms, and $R_2$ and $R_3$, which can be the same or different, are hydrogen, lower alkyl having from 1 to 4 carbon atoms, cycloalkyl having 5 or 6 carbon atoms, benzyl or benzyl substituted on the benzene ring with alkyl having from 1 to 4 carbon atoms, alkoxy having from 1 to 3 carbon atoms, chloro, bromo or nitro, or

form a saturated heterocyclic ring selected from the group consisting of pyrrolidine, piperidine and morpholine, and pharmacologically acceptable acid addition salt thereof.

2. A compound as set forth in claim 1 wherein a is 0.
3. A compound as set forth in claim 1 wherein $R_1$ is hydrogen or methyl.
4. A compound as set forth in claim 1 wherein the acid is an organic acid.
5. A compound as set forth in claim 1 wherein the acid is a mineral acid.
6. A compound as set forth in claim 5 wherein the mineral acid is a hydrohalogenic acid.
7. A pharmaceutical composition which comprises as an active ingredient a pharmaceutically effective amount of at least one of the compounds as claimed in claim 1 and at least one pharmceutically acceptable inert carrier or diluent.
8. A compound as claimed in claim 1, namely, N-(1-tricyclo[4.3.1.1$^{2,5}$]undecyl)-2-aminoacetamide hydrochloride.

* * * * *